United States Patent [19]

Ziets et al.

[11] 4,093,490
[45] June 6, 1978

[54] METHOD OF MAKING VAGINAL DIAPHRAGM

[75] Inventors: George A. Ziets, Bound Brook; Bernard L. Williams, Martinsville, both of N.J.

[73] Assignee: Ortho Pharmaceutical Corporation, Raritan, N.J.

[21] Appl. No.: 792,383

[22] Filed: Apr. 29, 1977

[51] Int. Cl.² .................................................. B29F 1/00
[52] U.S. Cl. .................................... 156/245; 128/130; 156/285; 264/328
[58] Field of Search ............... 156/242, 245, 285, 293; 128/130, 131, 138 R, 285; 264/328

[56] References Cited

U.S. PATENT DOCUMENTS

| | | | |
|---|---|---|---|
| 3,545,439 | 12/1970 | Duncan | 128/130 |
| 3,899,564 | 8/1975 | Kessler et al. | 264/328 |
| 4,012,496 | 3/1977 | Schopflin et al. | 128/130 |

*Primary Examiner*—Caleb Weston
*Attorney, Agent, or Firm*—Benjamin F. Lambert

[57] ABSTRACT

This invention relates to an improved method of making a vaginal diaphragm. The diaphragm of the present invention is prepared from thermoplastic elastomers by means of injection molding.

7 Claims, No Drawings

METHOD OF MAKING VAGINAL DIAPHRAGM

The invention relates to an improved method of making a vaginal diaphragm. In particular, the present invention relates to diaphragms prepared from thermoplastic elastomers employing an improved injection molding technique.

A vaginal diaphragm commonly comprises an imperforate cup-shaped member made of a thin rubber-like material having a round, somewhat stiff but resilient rim. A spring is generally incorporated therein to maintain the shape of the diaphragm. Opposite sides of the rim can be folded together to form a compact diaphragm unit to facilitate insertion of the diaphragm into the vagina. The presence of the spring causes the diaphragm to assume a "bow" shape when folded. Without the spring the diaphragm would not be rigid enough to form the "bow" shape and would, therefore, be difficult to insert. When the folded diaphragm is fully inserted within the vagina, release of the diaphragm establishes the round shape of the diaphragm rim which then makes the sealing engagement with the inner walls of the diaphragm around the cervix, which fits within the diaphragm. The seal formed by the rim prevents ingress of sperm cells into the cervical region.

Present day diaphragms generally consist of a latex membrane having a metal spring or latex ring encapsulated in latex. Latex has certain properties which make it less than ideal as a material from which to make diaphragms. Latex materials by their very nature have a tendency to form pinholes in a free film such as that commonly used in the preparation of diaphragms. Rubber or rubber-like materials such as polyethylene and polyvinyl chloride have also been employed in the making of diaphragms but these too have certain disadvantages connected with their use. There is a need, therefore, for a material which can be made into free films for use in the fabrication of diaphragms which has the resiliency and flexibility of the prior art materials but does not have their inherent disadvantages.

One object of the present invention is to provide a vaginal diaphragm comprised of a thermoplastic elastomer having sufficient resiliency and flexibility to allow easy insertion of the diaphragm by the user without the aid of an instrument.

A second object of the invention is to provide an improved method of making pinhole-free diaphragms from thermoplastic elastomers.

These and other objects of the invention will be better understood upon reference to the following description.

In accordance with the present invention, there is provided a method of making a diaphragm comprising a film and rim made from a thermoplastic elastomer. Both the film and the rim may be made from the same or different thermoplastic elastomers. The film and the rim are formed individually and then combined into a single unit. The properties of thermoplastic elastomers are such that the rim once formed has the required rigidity but remains freely flexible. When the diaphragm is in position, the rim lies flat against adjacent organ surfaces and its flexibility permits it to accommodate itself to the contour of the surfaces. However, the rim is rigid enough to hold the cup portion of the diaphragm in its extended position and is completely flexible throughout. This not only adds to the comfort, but ensures the proper fitting of the diaphragm. The squeezing of the rim causes the diaphragm to assume a "bow" shape, which is also arcuate. When the rim is thus squeezed together, the cup takes on something of a draped condition between the two ends of the bow formed by the rim. This facilitates insertion and proper placement of the diaphragm.

In the fabrication of a diaphragm, according to the preferred method of this invention, the first step involves the formation of the rim portion. The rim is prepared by injection molding the thermoplastic elastomer. As indicated above, it is preferred that the diaphragm be capable of assuming a "bow" shape when the rim is squeezed on the sides to facilitate easy insertion. Conventional injection molding comprises side injection of softened polymeric material into the ring mold. This results in only two stress points in the ring thus making it difficult to form the bow on all sides when squeezing the rim of the diaphragm. According to the present invention, the rim is prepared by center injection molding, i.e. the softened thermoplastic elastomer is injected from the center of the mold through a number of outlets simultaneously. It is preferred to use four or more outlets in this step. This procedure results in the formation of a multitude of stress points in the finished rim. Thus when the rim of the finished diaphragm is squeezed, the "bow" shape is obtained in each instance because of the more even distribution of the stress points around the rim. The temperature at which the molding step is carried out is not critical; however, it is preferred to heat the polymer to a temperature high enough to soften the material, but low enough to prevent chemical breakdown of the elastomer. The specific temperature employed in the molding step will depend upon the particular polymer employed and the time allowed for the mold to set. After formation of the rim, the flash is removed from the side and center portions of the rim prior to attaching the rim to the dome. The rim may be heated for a short period before placing it into the annular groove of the diaphragm mold used to form the dome. This can be accomplished by placing the rim in an oven at a temperature below the melting point of the thermoplastic elastomer; however, any suitable means can be employed to heat the ring. The preheating step is only a preferred step, however, and is not critical to the process. A film of the thermoplastic elastomer is then preheated on some suitable support to a temperature below its melting point prior to being placed on the dome portion of the mold. The film itself may be prepared by blow molding, by extrusion or casting or by other techniques known in the art. It is preferred to maintain the rim and mold at a temperature at which the elastomer is softened but below its melting temperature prior to bringing the mold in contact with the film. This step can be performed by heating the rim and the mold in a single heating unit or in separate units or in any other suitable fashion. To form the dome-shaped portion of the diaphragm, the mold and film are brought into contact with each other; the heated mold thus causes the film to conform to its dome-like shape and acts as a heat sealing element to seal the film to the preformed diaphragm ring. In an alternate step, either vacuum or pressure may be applied to the entire mold at the same time that the film comes into contact with the mold and the rim. In this way the dome forms a tight seal with the ring, and the resulting diaphragm is free of pinholes. A vacuum between 2 psi and 20 psi is suitable, although it is preferred to apply a vacuum of between 4 psi and 5 psi.

Where pressure is applied, a pressure between 1 mm. and 32 mm. is suitable, although it is preferred to apply a pressure between 20–25 mm. Alternatively, the rim and dome may be joined together by means of other techniques such as, for example, by radio frequency techniques or by solvent or adhesive bonding.

The mold and the diaphragm are held in place only momentarily after the sealing has been accomplished, generally in the order of 25–60 seconds. The fusing or sealing of the membrane to the rim portion of the diaphragm is accomplished almost instantaneously on contact, and the mold is separated from the diaphragm. The formed diaphragm is then quenched by techniques known in the art which cause the dome-shaped portion of the diaphragm to set in the shape of the mold.

Any thermoplastic elastomer may be employed to form the films used to prepare the diaphragm of the present invention. However, in order to achieve a certain degree of softness for the dome and flexibility for the rim, it is preferred to use thermoplastic elastomers having an average Shore A hardness of about 50 to about 90. The most preferred range is from about 75 to 90. However, softer or harder thermoplastic elastomers can be employed; they can be compounded with compatible polymers such as ethylene propylene elastomers, plasticized polyvinyl chloride, or acrylonitrile-butadiene-styrene terpolymer, for example, to produce the desired modulus. Suitable thermoplastic elastomers which may be employed in preparing the diaphragms include styrene-butadiene block copolymer, styrene-isoprene block copolymer, ethylene-vinylacetate, ethylene propylene copolymer and ethylene propylene terpolymer. The preferred thermoplastic elastomers are the thermoplastic polyurethanes having a polyester or polyether linkage. Suitable thermoplastic polyurethanes which can be employed include Pellethane (an Upjoin polyether based urethane elastoplastic polymer), Cyanoprene (an American Cyanamid Company fully-reacted polyester or polyether type urethane thermoplastic elastomer), Estane (a B. F. Goodrich Company thermoplastic polyurethane made from polyester or polyether based urethanes), Roylar (a Uniroyal Company thermoplastic polyurethane elastomer), Rucothane (a Hooker Chemical Company polyurethane elastomer), Q-Thane (a Quinn Company polyurethane thermoplastic elastomer) and Texin (a Mobay Chemical Company polyurethane thermoplastic elastomer).

The diaphragm prepared by the process of the present invention consists of a dome-shaped film and an injection molded rim both made from a thermoplastic elastomer. The dome-shaped film and the rim can be made from the same elastomer or different thermoplastic elastomers. In one embodiment of the diaphragm, a spring comprising a flexible polymeric ring or flexible metal coil is embedded in the rim to give it added rigidity. One suitable form of metal coil comprises a helical spring which is bent into an annulus. The ends of the spring can be joined by any suitable means. They may be intermeshed, welded, or otherwise secured together so that the spring is annular. The metal coil, however, is an optional feature of the diaphragm since the physical properties of the thermoplastic elastomer are sufficient to give the rim and diaphragm the rigidity required to ensure proper fitting of the diaphragm.

Some changes may be made in the details of the procedure involved in the practice of the method of this invention and in the construction and parts of the apparatus used in carrying out the method and of the thermoplastic materials used in the preparation of the diaphragm without departing from the spirit and scope of the invention.

The following example illustrates the process for making a diaphragm from a thermoplastic elastomer:

(a) The thermoplastic resin (Pellethane #2363-90A) is heated at 115° F for 3 hours and is vacuum dried for an additional 2 hours. The resin is then heated at 410° F and the softened resin is center injection molded in a ring mold at a temperature of 155° F. The injection time is approximately 5 seconds. The rings is allowed to cure for 20 seconds after which the flash is removed from the center and the side.

(b) A sheet of thermoplastic resin (Pellethane #2363-80A) is cut into a 6-inch square, clamped on a clamping frame and heated at 460° F for 11 seconds. The ring formed in (a) above is first heated at 410° F for 90 seconds after which it is placed on the diaphragm mold. The ring and mold are preheated at 180° F for 11 seconds. The mold is then moved up into the film, and when the mold meets the film, vacuum is applied (25 mm./Hg.). The parts are held in place for 30 seconds after which the formed diaphragm is removed and placed in water for 30 seconds.

What is claimed is:

1. The method of making a diaphragm comprising center injection molding a rim from a thermoplastic elastomer, deforming a sheet of a thermoplastic elastomer into a dome at an elevated temperature, said sheet having a diameter greater than said ring, and sealing said dome to said ring, whereby a diaphragm is formed having a continuous rim integral with a flexible dome-shaped membrane.

2. The method of claim 1 wherein the rim is heat sealed to the dome.

3. The method of claim 1 wherein vacuum is applied during the sealing step.

4. The method of claim 1 wherein pressure is applied during the sealing step.

5. The method of claim 1 wherein the rim and dome are comprised of the same thermoplastic elastomer.

6. The method of claim 1 wherein the rim and dome are comprised of different thermoplastic elastomers.

7. The method of claim 1 wherein the rim and dome comprise a thermoplastic polyurethane having a Shore A hardness of between 50–90.

* * * * *